United States Patent [19]

Butler

[11] Patent Number: 5,116,347
[45] Date of Patent: May 26, 1992

[54] TICK REMOVER FOR PEOPLE AND ANIMALS

[76] Inventor: Robert B. Butler, R.D. 8, 650 Union Valley Rd., Mahopac, N.Y. 10541

[21] Appl. No.: 647,241

[22] Filed: Jan. 29, 1991

[51] Int. Cl.$^5$ .................................................. A61B 17/00
[52] U.S. Cl. ................................. 606/131; 606/205; 606/207; 606/210; 81/300; 81/418
[58] Field of Search .................. 606/131, 205–209, 606/210; 81/9.4, 318, 328, 415–420, 424.5, 300–315

[56] References Cited

U.S. PATENT DOCUMENTS

| 547,292 | 10/1895 | Ruppertz | 606/205 |
| 632,843 | 9/1899 | McGhee | 606/207 |
| 964,600 | 7/1910 | Adams | 81/9.4 |
| 1,077,672 | 11/1913 | vom Cleff | 81/415 |
| 1,107,210 | 8/1914 | Adams | 81/9.4 |
| 1,510,416 | 9/1924 | Pietz et al. | 606/205 |
| 1,725,638 | 8/1929 | Hellermann | 81/302 |
| 1,765,783 | 6/1930 | Young | 606/205 |
| 2,939,214 | 6/1960 | Andersson et al. | 81/416 |
| 3,184,838 | 5/1965 | Johnson | 81/418 |
| 4,041,740 | 8/1977 | Villazon | 81/418 |
| 4,213,460 | 7/1980 | Weiner | 606/131 |
| 4,442,837 | 4/1984 | Keatley | 606/131 |
| 4,554,848 | 11/1985 | Galletto | 81/318 |
| 4,938,764 | 7/1990 | Glaberson | 606/131 |
| 4,976,718 | 12/1990 | Daniell | 606/131 |

FOREIGN PATENT DOCUMENTS

| 1122303 | 11/1984 | U.S.S.R. | 606/208 |
| 1510843 | 9/1989 | U.S.S.R. | 606/208 |
| 658069 | 10/1951 | United Kingdom | 81/305 |

*Primary Examiner*—Stephen C. Pellegrino
*Assistant Examiner*—Glenn K. Dawson

[57] ABSTRACT

A simple hand-held implement for removing ticks and other ectoparasites or small undesirable objects from the cutaneous areas and clothing of humans and animals.

8 Claims, 2 Drawing Sheets

TICK REMOVER FOR PEOPLE AND ANIMALS

FIELD OF THE INVENTION

The invention relates in general to the field of preventive medicine, and particularly to the hygienic need to simply, safely, and comfortably remove ticks and other ectoparasites from the skin of humans, dogs, and other animals, including those found in hairy or furry areas where such organisms are difficult to find and difficult to remove.

BACKGROUND OF THE INVENTION

The food of a tick is human or animal blood, which it obtains by burying its snout in the flesh of its host and sucking until its highly elastic body is engorged with the red fluid. Due to the viruses and bacteria on or in ticks' bodies which can be transmitted to the host as they feed, these organisms cause Lyme disease, Rocky Mountain spotted fever, Colorado tick fever, tularemia, relapsing fever, tick paralysis, and ricksettial diseases; and Lyme disease, anaplasmosis, babesiosis, equine and St. Louis encephalitis, Q fever, spirochetosis, and toxoplasmosis in animals. At 400×magnification, the snout of a tick resembles the nose of a sawfish: it has a long, straight, blade-like shape with a row of ten to twelve barb-like teeth on each side. Through this hollow proboscis passes the blood which the tick sucks from its host. Most importantly, when the tick retracts this apparatus after becoming engorged, it autonomically regurgitates a small portion of its blood meal, leaving it behind in the flesh of the host. In the case of Lyme disease, medical research has recently found that the transmitter of the disease is a spirochete that lives in the tick's hind gut; and it is only during the tick's autonomic reflex process of regurgitation upon removing its proboscis that the possibly present spirochete is injected into the host. In fact, it is now known that most sufferers of Lyme disease contracted the illness not because they were bitten by a tick, but because the tick was improperly removed. This new medical knowledge also indicates that the most common methods of removing ticks—such as with the fingers, with tweezers, by applying heat, dousing the parasite with a chemical, or rotating the parasite about its longitudinal axis in efforts to dislodge its imbedded proboscis—are undesirable, and in some cases can actually promote the spread of this and other tick-borne diseases.

For example, grabbing the tick with one's fingers is undesirable, as this squeezes its posterior which is another way of injecting the spirochete into the host. Also, this method of removal can pull out some of the host's hair to its considerable discomfort and pain. Furthermore, touching the parasite is considered by many as repulsive, and this method of removal can also spread diseases borne on the tick's surface. Finally, when removing a tick by hand, a person usually employs his or her free hand to hold a tissue to receive the removed tick, and in so doing often loses the location of the wound in the possibly thick hair of the host, then subsequently has trouble relocating the wound for purposes of examination and applying medication.

Using tweezers to remove a tick is undesirable, as the hand holding them usually obstructs one's view of the invading organism during use, and considerable dexterity is required to place their two tiny gripping surfaces around the feeding parasite in the host's possibly thick fur; and even then the closing of the tweezer's jaws, especially if their opposing faces are flat or nearly so, will pinch the tick's posterior and inject the host with a portion of its blood meal while at the same time pulling hair from the host. Also, using tweezers can lead to dropping the tick from the jaws as the implement's legs spring open as it is laid aside, and, if the second hand is required for such disposal, subsequent difficulty in relocating the host's wound for purposes of examination and applying medication.

Applying heat is undesirable, as when the tick backs away from the host in efforts to escape the burning or the fumes, the organism once again activates its autonomic reflex process of regurgitation which can inject the spirochete into the host. Also, this activity usually requires both hands of the remover, can burn the host and even the remover, and often renders the tick incapable of subsequent analysis by public health officials.

Applying Vaseline, kerosene, chloroform, or other chemical also activates the autonomic reflex process of regurgitation of the parasite as it tries to back away from the host in efforts to get air, not to mention likely irritation to the host and subsequent need to thoroughly clean the wound.

Finally, rotating an imbedded parasite about its longitudinal axis in efforts to dislodge it is undesirable, as this will surely tear the tick's posterior from its lengthy barbed snout that is buried in the host, resulting in certain damage to tick and host.

All the above methods do not address the urgent problem of simply, safely, and comfortably removing a tick from its host. Furthermore, none of the above methods allow the remover's other hand to remain free at all times to calm the host and maintain location of the tiny wound. Finally, each of the above methods tend to hide or obscure the invading organism from view during some part of its removal.

PRIOR ART

Considering any prior art that might negate the patentability of the disclosed invention, the inventor performed a search of all patents of several class/subclasses 29/248, 43/102, 43/107, 43/110, 43/121, 43/133, 43/134, 43/138, 43/143, 43/144, 119/87, 128/399, 219/230, 606/131, 606/205, 606/211, and D8/52—a total of 779 patents in all. Of these, only two were remotely similar to the disclosed invention; and even they were fundamentally different as described below:

Weiner, in U.S. Pat. No. 4,213,460, describes a tick removing forceps that is [from the abstract] "for removing a parasitic organism attached to the skin of a host animal." An analysis of Weiner's claims proves that his invention is very different than the disclosed invention in several respects. First, each of his four broadest claims 1, 8, 20 and 21 begins by stating that his invention comprises a forceps, which is a tong-like instrument whose legs are joined at the opposite end from their mutually opposed gripping means; and this manner of leverage differs from the corresponding physics of the disclosed invention. Second, each of Weiner's four basic claims states that his invention comprises in (1) "heating means when said gripping means are engaged with said parasitic organism . . . " or (8) "an electrical resistance heating element provided on an internal surface of one of said gripping members in a position to apply heat to the enclosed portion of said tick . . . " or (20) "a flexible reservoir included in said handle portion of said forceps for containing a supply of a relaxant chemical agent . .

." or (21) "a flexible reservoir affixed to said handle portion of said forceps for containing a supply of a relaxant chemical agent . . . "; whereas the disclosed invention has no heating, electric, or chemical apparatus whatsoever. Third, each of Weiner's four broadest claims states that his invention comprises in (1) "control means for activating said heating means . . . " or (8) "actuator means . . . to apply heat to said tick . . . " or (20) or (21) "an operator . . . can apply pressure to said reservoir . . . "; whereas the disclosed invention has no control, actuator, or operator means whatsoever. Thus each of these elements in Weiner's broadest claims, and therefore all elements in his dependent claims, teaches away from the essential nature of the disclosed invention, and for each of these reasons exclusive of the others the disclosed invention is patentable over Weiner.

Keatley, in U.S. Pat. No. 4,442,837, describes a tweezers for the removal of parasites from animals. An analysis of Keatley's claims proves that his invention is also very different than the disclosed invention in several respects. First, Keatley's one independent claim begins by stating that his invention comprises a tweezers, whose "flexible legs" are "fixedly joined at their upper ends"; and this manner of leverage differs from the corresponding physics of the disclosed invention. Second, Keatley's broadest claim concludes by stating that his invention comprises "a knob fixed to the top of said thumb ring to be engaged . . . to turn said legs about a longitudinal axis between them"; whereas operation of the disclosed invention involves no longitudinal rotation whatsoever of the captured organism. Thus each of these elements in Keatley's broadest claim, and therefore all elements in his dependent claims, teaches away from the essential nature of the disclosed invention. Third, the section of Keathley's patent titled Background of the Invention states that "by rotating the tick smoothly, it is more easily dislodged from the host animal," a premise which if not initially false has subsequently been proven by medical authorities to be erroneous. Yet throughout Keatley's specification (see his Object of the Invention, col. 1, line 28-31; Summary of the Invention, col. 1, line 50-52; and Description of a Preferred Embodiment, col 2, line 59-62) he bases the overall success of his invention on this erroneous premise. In particular, in col. 2, line 60-62, he describes the tick as being "rotated . . . causing it to lose its hold without damage to itself or to the host animal." This statement simply isn't true, as due to the long rows of barb-like teeth on each side of the tick's proboscis any longitudinal rotation of the tick's body would surely tear its posterior from its imbedded proboscis, resulting in the contrary occurrence of obvious damage to both tick and host. Thus Keatley, by his own erroneous premise and substantiation, has invented a tick remover that is medically undesirable, whose essential nature teaches away from the medically desirable nature of the disclosed invention. Thus, for each of these reasons exclusive of the others, the disclosed invention is patentable over Keatley.

SUMMARY OF THE INVENTION

The best way to remove a tick imbedded in its host is by grasping the parasite about its neck, then gently pulling its hard exoskeletal proboscis directly backward through the soft flesh around it in a way that does not involve human contact with the parasite or activate its autonomic reflex process of regurgitation. Accordingly, the disclosed invention is a plier instrument made of a structurally appropriate material (such as metal or plastic) whose uniquely designed jaws may be opened easily and placed quickly and accurately around a tick or other parasite whose head is imbedded in the skin of the host; then the jaws are closed around the parasite in the vicinity of its dorsal scutum (the narrow area between its imbedded snout and possibly swollen posterior), and finally the tick is removed by pulling the implement with one hand directly from the host's skin, while the other hand is free at all times to calm the host and maintain location of the wound for subsequent examination and applying of medication.

A principle feature of the invention is the small gap that exists between its uniquely designed jaws when they are closed around a tick. As the dorsal scutum of a tick is usually about twelve thousandths (0.012) of an inch thick when empty of blood but can be as thin as eight thousandths (0.008) of an inch in some adult subspecies, and because human and dog hairs range between one and three thousandths (0.001-0.003) of an inch thick, the mutually opposed jaws when closed have a gap of about six thousandths (0.006) of an inch between their edges, which allows the host's hair to slide freely through the jaws while at the same time the jaws grip a tick securely during its capture and removal from the host. At any time the user may relax or increase his or her grip on the implement, with its jaws responding immediately to the user's desire to maintain optimum performance.

Another feature of the invention is that the edges of its mutually opposed jaws are dull and have a convex-shaped cross section along their length, enabling the jaws to graps the invading organism securely without severing its posterior from its head. This also allows a tick to remain securely in the implement's jaws whether the parasite's body is empty of blood or fully engorged, or whether the user grips the implement tightly or lossely.

Another feature of the invention is that, contrary to tweezers or other instruments whose range of contact with the invader is very small, the edges of its two jaws are long enough to allow the user to locate them quickly and easily around a tick found on the skin of its host, even if the host's hair is long, thick, matted, or wet.

Another feature of the invention is that its jaws' bottom sides are bevelled upward from their edges, enabling the jaws' edges to nestle snugly against the host's skin as they close upon the invader in the narrow area between its imbedded head and possibly swollen posterior.

Another feature of the invention is that its jaws' edges incline upward from base to tip, enabling them to nestle against the host's skin while its handles remain far enough above the host for the user's hand to grip them comfortably. This incline also prevents the unsanitary head of a removed parasite awaiting disposal from touching a flat surface upon which the implement has been laid.

Another feature of the invention is that its jaws' tips are pointed to facilitate its passage through the possibly dense hair of the host as the opened jaws approach a tick, yet the tips are not so sharp that they could injure the host or tear a pocket the implement might be carried in.

Another feature of the invention is that the inner and upper surfaces of the jaws have a concave configuration which, when the jaws come together, forms an ample cavity for cradling without squeezing the posterior of a fully engorged tick during and after removal from the host and prevents it from later being dropped or lost.

Another feature of the invention is that the open design of its cradle combined with the generally flat design of its other parts does not obstruct one's view of a tick found on the skin of its host during any phase of the parasite's capture and removal.

Another feature of the invention are the stops located along the points of contact between its two handles, whose mating surfaces maintain the small gap that exists between the jaws when its handles are squeezed.

Another feature of the invention are the guides also located along the points of contact of its two main pieces, whose overlapping surfaces make its jaw edges align correctly against each other when they close.

Another feature of the invention are its contoured handles, whose easily graspable shape allows the implement's other features to be utilized comfortably and quickly.

Another feature of the invention are the reverse stops located near the front of the handles and equidistantly outside the jaw's outer surfaces, which prevent the jaws from opening any wider than necessary during use.

Another feature of the invention are the holes in the area between the handles and the stops, which in addition to making the implement lighter allow it to be hung on a hook or mounted on a string or other carrying medium.

The principal advantage of the invention is that it allows one to guide the implement quickly and easily through the host's possibly hairy skin toward a feeding tick, then remove the parasite simply and safely at minimum discomfort to the host.

Another advantage of the invention is that only one hand is required to use it during all phases of operation, leaving the other hand free to calm the host, manipulate the flesh around the wound during removal of the parasite, and maintain location of the tiny wound during subsequent inspection of the parasite and placing it aside for disposal.

Another advantage of the invention is its jaws' ability to retain their position after the implement is laid aside, thus keeping the removed parasite from falling away and possibly escaping.

Another advantage of the invention is that it can be washed easily after being used.

Another advantage of the invnetion is that its jaws can be used to grasp a tiny nonengorged tick walking or resting on the skin or clothing of its host, or even fleas, body lice, other ectoparasites, and also cockleburrs and large splinters and other undesirable matter appearing on the body or clothing of the host.

Another advantage of the invention is that it is safe and simple to operate by an adult or responsible child.

Another advantage of the invention is that its smallness and light weight allow it to be slipped into a pocket and carried on hikes into remote environments, or easily placed in a purse, toilet kit, or first aid kit.

Another advantage of the invention is that it requires no batteries or accessory equipment of any kind.

In these ways, the disclosed invention may greatly improve present methods of removing ticks and similar parasites from humans and animals. In so doing, the implement may also remove the anxiety that many have about performing such operations. Finally, it may allow people to feel more comfortable about enjoying the many advantages that outdoor environments have to offer.

BRIEF DESCRIPTION OF THE DRAWINGS

These and other aspects, features, and advantages of the disclosed invention may be better understood by a detailed description of the preferred embodiment of the invention as revealed by the following drawings, in which.

DESCRIPTION AND OPERATION OF THE PREFERRED EMBODIMENT OF THE INVENTION

Figure 1:
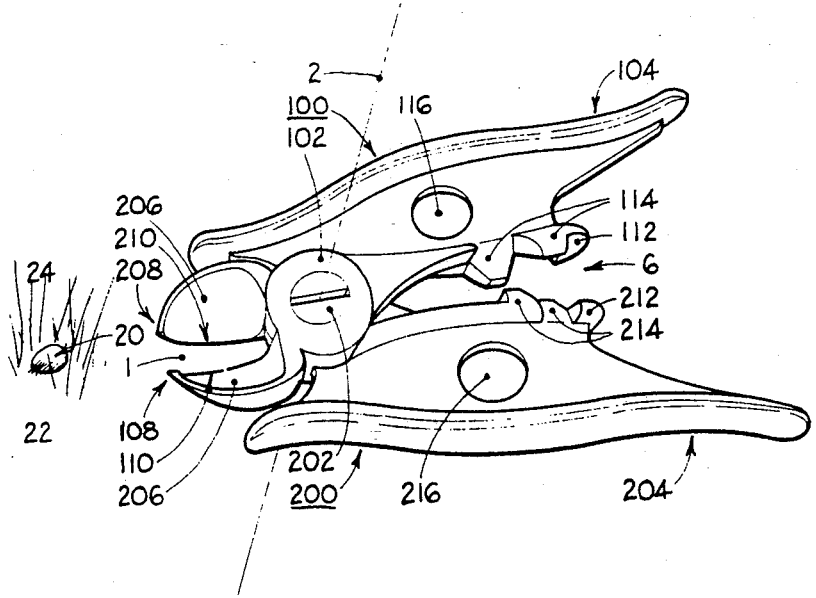
FIG. 1 is a general perspective view of the invention as it approaches a tick feeding on its host.

Referring to FIG. 1 of the drawings, the invention consists of two basic pieces 100 and 200, each piece being made of a structurally appropriate material (such as metal or plastic), with each piece being connected to the other at a central pivot called the fulcrum 2. The two handles 104 and 204 are of a smoothly contoured construction that fits comfortably in the user's palm, and both jaw tips 108 and 208 are pointed to facilitate the passage of the implement through the hair of the host but not so sharp as to prick the host's skin during such movement. Located between the handles 104 and 204 at the base 6 of the handles are the stops 112 and 212, two smooth surfaces which mate when the handles 104 and 204 are squeezed to maintain the proper gap 1 between the jaws' bevelled edges 110 and 210, and the guides 114 and 214, which overlap when said handles are squeezed to keep said bevelled jaw edges properly aligned.

Figure 2:
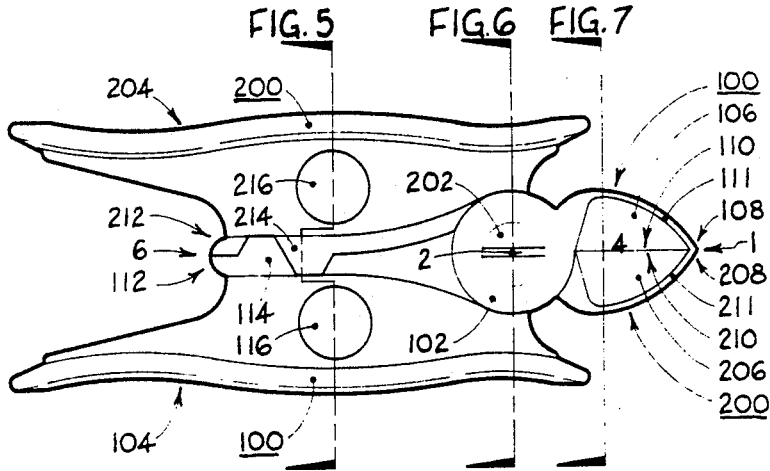
FIG. 2 is a top view of the invention with its jaws closed, showing the cavity for cradling a captured parasite and general arrangement of the handles.

Referring to FIG. 2, in this top view the invention's handles 104 and 204 are closed, thus closing the mutually opposed jaws 106 and 206 opposite the fulcrum 2. In this position the stops 112 and 212 come together to maintain the proper gap 1 between the jaw edges 110 and 210, with the gap being narrow enough to firmly grasp a tick, yet wide enough to allow any hair 24 of the host 22 to slide through the jaws as the tick 20 is being pulled away. Also in this position the guides 114 and 214 along the stops 112 and 212, overlap to ensure that the jaws align when closed. This view also shows the axle 202 inside the hub 102, as well as hole 116 in piece 100 and hole 216 in piece 202. Finally this view shows the cradle 4, the cavity between the jaws 106 and 206 where the posterior of a captured tick 20 is lodged as its head is being removed from the skin of the host 22, and where the parasite is held during subsequent removal from the host and transportation to disposal. This view also shows rims 111 and 211 that form the upper edge of cavity 4.

Figure 3:
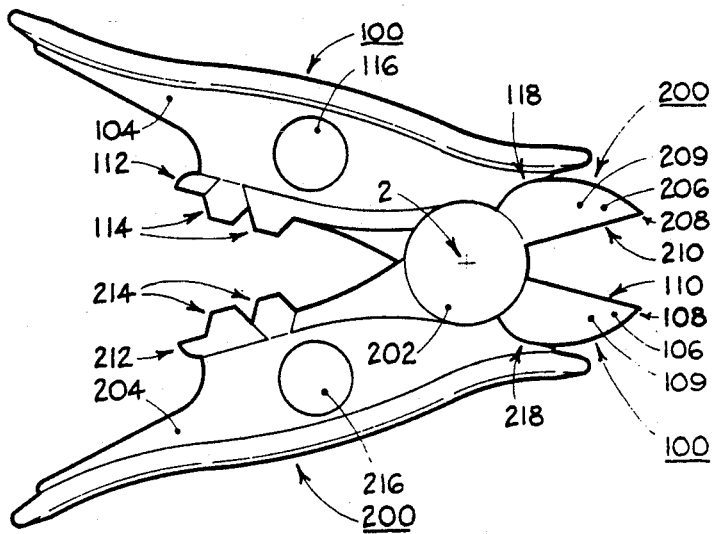
FIG. 3 is a bottom view of the invention with its jaws open, showing the underside of the jaws' bevelled edges and the interlocking guides along the stop.

Referring to FIG. 3, in this bottom view the invention's handles 104 and 204 are fully open, thus opening the jaws 106 and 206. In this position the outside of said jaws rest against the reverse stops 118 and 218, preventing said jaws from opening any farther than necessary. Also shown are the bevelled undersides 109 and 209 of the jaws 106 and 206, whose surfaces nestle against the skin of the host so the jaw edges 110 and 210 can close firmly around the neck of the tick before removal. This view also profiles the overlapping guides 114 and 214 protruding from the stops 112 and 212.

Figure 4:
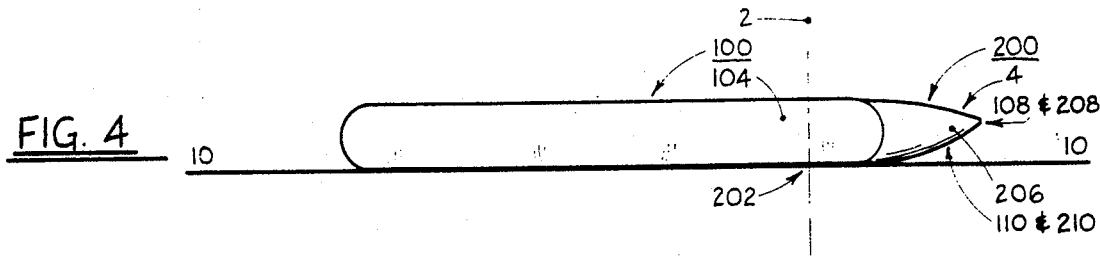
FIG. 4 is a side view of the invention as it lays on a flat surface, showing the upward incline of the jaws' undersides toward their tips.

Referring to FIG. 4, this is a side view of the invention as it rests on a flat surface 10, showing how the jaw edges 110 and 210 incline upward from the hub 202 to the tips 108 and 208 to prevent the unsanitary head of a removed parasite from touching the surface 10 while remaining firmly grasped in the jaws 106 and 206. This view also shows the outer surface of the comfortably contoured handle 104.

Figure 5:
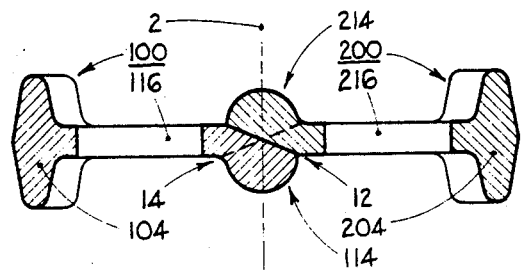
FIG. 5 is an enlarged sectional view cut through the invention's guides located along the stop, showing how the guides overlap when the handles are closed, taken along the lines 5—5 in FIG. 2.

Referring to FIG. 5, this sectional enlargement shows how one pair of the overlapping guides 114 and 214 mate in closed position, their seam being solid line 12. Beyond them exist the other pair of guides 114 and 214 in similar position, their seam being dotted line 14. Thus one pair of guides 114 and 214 prevents the jaw edges 110 and 210 from nonaligning in one lateral direction, and the other pair prevents the jaw edges from nonaligning in the opposing lateral direction. Depending on the means of manufacturing, this alignment may also be achieved with a mating tongue and groove surface or one of several other overlapping means. This view also profiles the hole 116 in handle 104 and hole 216 in handle 204, as well as cross sections of handles 104 and 204.

Figure 6:
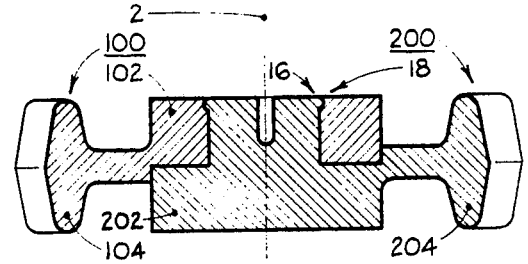
FIG. 6 is an enlarged sectional view cut through the invention's fulcrum and showing the hub-axle assembly, taken along the lines 6—6 in FIG. 2.

Referring to FIG. 6, this sectional enlargement shows the assembly at the fulcrum 2; in particular how the axle or other connecting means 202 fits into the hub or other receiving means 102 to allow pieces 100 and 200 to rotate smoothly against one another as the handles 104 and 204 operate jaws 106 and 206. In this embodiment of the invention, at the top of the hub-axle assembly is shown a mating knurl and groove, knurl 16 encircling axle 202 and groove 18 encircling hub 102, with said surfaces holding pieces 100 and 200 together after they have been snapped into place. Depending on the means of manufacturing, there are several other methods of connecting pieces 100 and 200 to maintain a snugly rotatable connection during subsequent use, such as riveting, staking, screwing, installation of spring or rubber washer, etc.

Figure 7:
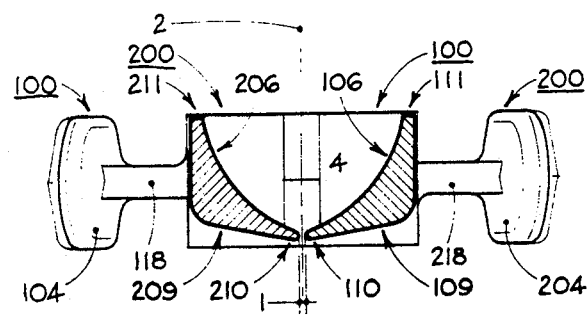
FIG. 7 is an enlarged sectional view cut through the invention's jaws, showing the thin gap and alignment between them when closed, taken along the lines 6—6 in FIG. 2.

Referring to FIG. 7, this sectional enlargement shows the jaws 106 and 206 in closed position, profiling their bevelled undersides 109 and 209 as they slope upward from the narrow gap 1 between the jaw edges 110 and 210 to enable said jaws to nestle against the skin of the host 22 so they can grasp a tick 20 in the narrow area between its buried proboscis and possibly swollen posterior. Above the jaws 106 and 206 is the cradle 4, whose lower concave surfaces slope shallowly enough to enable the jaw edges 110 and 210 to be placed around the neck of a feeding tick without pinching its posterior, and with said cavity being amply sized to hold a fully engorged tick and having rims 111 and 211.

Figure 8:
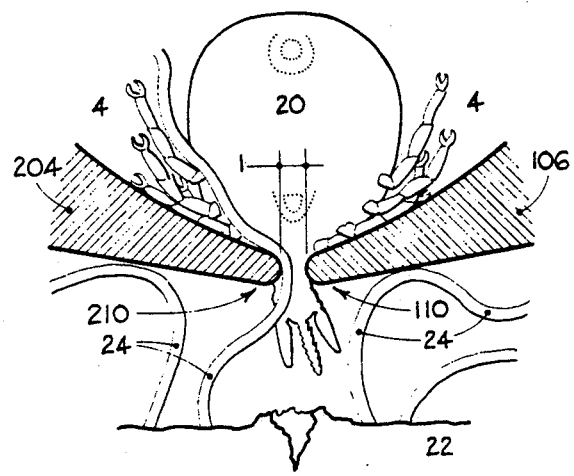
FIG. 8 is a greatly enlarged view of the jaw portion of FIG. 7, showing how a hair can slide freely through the thin gap between the aligned jaws while at the same time an engorged tick is held securely as the invader is pulled away from the host.

Referring to FIG. 8, this sectional view is a great enlargement of the lower jaw portion of FIG. 7, showing jaws 106 and 206 as they allow human or dog hairs 24 to pass through the narrow gap 1 between the jaw edges 110 and 210 while at the same time said dull edges with their convex cross sections grip a tick around its neck without cutting it as it is being drawn away from the host 22.

When the operator has seen or felt a tick 20 in the hair or fur of the host 22, he or she grasps the implements' handles 104 and 204 with one hand, opens said handles which opens the jaws 106 and 206, and thrusts the jaw tips 108 and 208 into the hair 24 toward the tick 20, moving the jaws 106 and 206 by sight or feel until their open edges 110 and 210 lie on each side of the target tick 20. The operator nestles the bevelled undersides 109 and 209 of jaws 106 and 206 against the host's skin 22 while squeezing the handles 104 and 204, making the mutually opposed jaw edges 110 and 210 close around the tick 20 in the vicinity of its neck, thus forcing its posterior to become lodged in cradle 4. These opening and closing actions occur in a way that is immediately responsive and accurately controlled with minimal effort on the part of the operator, while at all times allowing the target tick 20 to remain in full view as much as the host's hair will permit. Then the operator, holding the jaws 106 and 206 closed, gently but firmly pulls the handles 104 and 204 directly away from the host 22 and in so doing retracts the imbedded head of the tick 20 from the host's skin 22, during which time any hair 24 around the wound passes freely through the gap 1 between the jaw edges 110 and 210 of the jaws 106 and 206. After the implement is free of the host, the user continues to hold the handles 104 and 204 closed while transporting the tick 20 in the cradle 4 to its place of disposal. After the tick's disposal, all surfaces of the jaws 106 and 206 can be cleaned in normally soapy water.

As is apparent from the foregoing specification, the invention provides a novel and greatly improved method of removing ticks from humans and animals. Furthermore, using the invention requires only one hand, allowing the user's other hand to remain free to calm the host, manipulate the flesh around a located parasite for easier removal, and maintain location of the wound while the removing hand holds the parasite up for inspection and subsequently lays it aside. Finally, the invention does not obstruct one's view of the tick while being used, prevents the parasite from being touched, can be cleaned after use, is simply constructed with a minimum of parts, and requires no additionally connected parts or equipment.

Although the invention has been described in a preferred form with a certain degree of particularity, it is understood that the present disclosure of this preferred embodiment has been made only by way of example, and that numerous changes in construction details and the combination and arrangement of its various parts may be resorted to without departing from the spirit and scope of the invention as hereinafter claimed; and it is intended that the patent shall cover, by suitable expression in the appended claims, whatever features of patentable novelty that exist in the invention disclosed.

What is claimed is:

1. A plier for removing ticks from humans and animals comprising two rotatably interconnected mating halves, said plier having a pivot located between two mutually opposed jaws at one end of the plier and two mutually opposed handles at the other end of the plier, so that when said handles are squeezed said jaws are enabled to engage a tick, with said tick having a snout imbedded in said human or animal, a possibly swollen posterior, and a narrow area between said imbedded snout and possibly swollen posterior, with (A) said mutually opposed jaws being similar in shape and having thin co-operating jaw edges which coalign along substantially their entire length, with said jaw edges having a base at an end nearest said pivot and a tip at an end farthest from said pivot, with said jaw edges curving slightly upward in side profile from said base to said tip, and said jaw edges being dull, non-cutting, non-overlapping, and having convex-shaped cross sections along substantially their entire length, said jaw edges forming a thin gap between them when they engage said tick, with said thin jaw edge gap adapted to be approximately as wide as said tick's narrow area between its imbedded snout and possibly swollen posterior;

(B) said mutually opposed jaws curving upward in a direction away from said coaligning jaw edges to form a cavity between said jaws when said handles are squeezed, with said cavity being configured to loosely hold a fully engorged tick, said cavity having a curved upper rim which is substantially thinner than said cavity's width, said cavity having no opening below said rim other than said thin jaw edge gap when said jaw edges engage said tick; and (C) said mutually opposed handles having integrally formed co-operating stops between said handles, with said stops consisting solely of two mutually opposed surfaces that are nonadjustable, have only one setting, and have no movable or separable parts, said stops having a length that is substantially greater than their maximum width, and said stops serving to maintain said thin jaw edge gap when said jaw edges engage said tick when said handles are squeezed.

2. A plier for removing ticks from humans and animals according to claim 1 wherein said stops include overlapping guides for maintaining coalignment of said jaw edges when said handles are squeezed.

3. A plier for removing ticks from humans and animals according to claim 1 wherein each of said handles has an opening adapted to receive a hanging means.

4. A plier for removing ticks from humans and animals according to claim 1 wherein each of said handles has an outer portion having a wavy shape that conforms to the palm of the hand.

5. A plier for removing ticks from humans and animals comprising two rotatably interconnected mating halves, said plier having a pivot located between two mutually opposed jaws at one end of the plier and two mutually opposed handles at the other end of the plier, so that when said handles are squeezed said jaws are enabled to engage a tick, with said tick having a snout imbedded in said human or animal, a possibly swollen posterior, and a narrow area between said imbedded snout and possibly swollen posterior, with (A) said mating halves being constructed of a slightly resilient material;

(B) said mutually opposed jaws being similar in shape and having thin co-operating jaw edges which coalign along substantially their entire length, with said jaw edges having a base at an end nearest said pivot and a tip at an end farthest from said pivot, with said jaw edges curving slightly upward in side profile from said base to said tip, and said jaw edges being dull, non-cutting, non-overlapping, and having convex-shaped cross sections along substantially their entire length, said jaw edges forming a thin gap between them when they engage said tick, with said thin jaw edge gap adapted to be approximately as wide as said tick's narrow area between its imbedded snout and possibly swollen posterior;

(C) said mutually opposed jaws curving upward in a direction away from said coaligning jaw edges to form a cavity between said jaws when said handles are squeezed, with said cavity being configured to loosely hold a fully engorged tick, said cavity having a curved upper rim which is substantially thinner than said cavity's width, said cavity having no opening below said rim other than said thin jaw edge gap when said jaw edges engage said tick; and (D) said mutually opposed handles having integrally formed co-operating stops between said handles, with said stops consisting solely of two mutually opposed surfaces that are nonadjustable, have only one setting, and have no movable or separable parts, said stops having a length that is substantially greater than their maximum width, and said stops serving to maintain said thin jaw edge gap when said jaw edges engage said tick when said handles are squeezed.

6. A plier for removing ticks from humans and animals according to claim 5 wherein said stops include overlapping guides for maintaining coalignment of said jaw edges when said handles are squeezed.

7. A plier for removing ticks from humans and animals according to claim 5 wherein each of said handles has an opening adapted to receive a hanging means.

8. A plier for removing ticks from humans and animals according to claim 5 wherein each of said handles has an outer portion having a wavy shape that conforms to the palm of the hand.

* * * * *